United States Patent [19]

Mason

[11] Patent Number: 4,551,095
[45] Date of Patent: Nov. 5, 1985

[54] ATTACHMENT OF HERBST MECHANISM TO MAXILLARY ARCH

[76] Inventor: Charles W. Mason, 295 Kirby La., Bigfork, Mont. 59910

[21] Appl. No.: 696,556

[22] Filed: Jan. 30, 1985

[51] Int. Cl.$^4$ ............................................... A61C 3/00
[52] U.S. Cl. ........................................ 433/19; 433/22
[58] Field of Search ..................... 433/19, 23, 17, 18, 433/22

[56] References Cited

U.S. PATENT DOCUMENTS

| 626,476 | 6/1899 | Angle | 433/17 |
|---|---|---|---|
| 2,959,856 | 11/1960 | Gurin | 433/22 |
| 3,158,934 | 12/1964 | Waldman | 433/19 |
| 3,353,271 | 11/1967 | Blechman | 433/18 |
| 3,690,003 | 9/1972 | Gerber | 433/19 |
| 3,798,773 | 3/1974 | Northcutt | 433/19 |
| 3,815,238 | 6/1974 | Wallshein | 433/17 |
| 4,382,783 | 5/1983 | Rosenberg | 433/19 |
| 4,424,032 | 1/1984 | Howe | 433/19 |
| 4,462,800 | 7/1984 | Jones | 433/19 |
| 4,472,139 | 9/1984 | Rosenberg | 433/19 |

FOREIGN PATENT DOCUMENTS 1079955 12/1954 France .................................. 433/19

Primary Examiner—John J. Wilson
Attorney, Agent, or Firm—Stephenson and Boller

[57] ABSTRACT

Attachment of a Herbst mechanism to the maxillary arch by use of a headgear tube is disclosed. A shaft of a length greater than that of the tube passes completely through the tube so as to project both mesially and distally from the tube. The connection of the Herbst mechanism is to that portion of the shaft which projects distally from the tube. A stop is disposed on the shaft mesial of the tube to forcefully bear against the tube with a distally directed force when corrective force is being developed by the appliance. The stop in its preferred embodiment comprises an adjustable locking device which is selectively positionable on the shaft to set the amount of distal extension of the point of connection of the Herbst mechanism from the tube and thereby limit the distal movement of the lower arch and/or jaw.

18 Claims, 4 Drawing Figures

ATTACHMENT OF HERBST MECHANISM TO MAXILLARY ARCH

BACKGROUND AND SUMMARY OF THE INVENTION

This invention relates generally to orthodontic appliances and is particularly concerned with an improvement in attaching a Herbst mechanism to the maxillary arch.

Herbst mechanisms are used in treatment of orthodontic conditions where it is desired to use the natural jaw closure force to move the mandibular arch anteriorly. The usual form of Herbst mechanism comprises a pair of telescopically engaged members, i.e. a tube and a shaft, and usually an appliance contains two such mechanisms, one on each side of the arch. Each mechanism is disposed between the arches, and is attached to the maxillary arch at a more distal location than it is attached to the mandibular arch. In response to jaw closure, the telescopically engaged members of each mechanism assume a force applying position whereby an anteriorly directed force is exerted on the mandibular arch. This force may be developed by an interference between the telescopically engaged members which limits the extent to which the members can telescope and/or it may include a spring mechanism operatively arranged to develop force between the telescopically engaged members.

Various means of attachment of a Herbst mechanism to the respective arches are known. The attachment of a mechanism may be to one or more teeth of an arch. For example attachment to arch wires is a known technique. The arches may or may not be stabilized as a unit depending upon the specific treatment procedure for a particular patient.

The following patents relate to various known appliances:
U.S. Pat. No. 3,158,934
U.S. Pat. No. 3,654,702
U.S. Pat. No. 3,690,003
U.S. Pat. No. 3,798,773
U.S. Pat. No. 4,424,032
U.S. Pat. No. 4,462,800
French Pat. No. 1079955

The present invention is directed to a new and improved means for attaching a Herbst mechanism to the maxillary arch. It comprises a number of important advantages over prior types of attachment.

One important advantage of the invention is that ease of placement and removal of the appliance is enhanced. Much of the tedious work which is often associated with application of an appliance to a patient can be done extra-orally before intra-oral placement. After intra-oral placement, adjustments can be easily performed in a convenient and facile manner to correct midline, etc.

Another particular advantage is that the invention can readily fit all standard head gear tubes without any modification. In the case of an emergency involving breakage or the like, the attachment can be relatively easily replaced.

Since in the preferred embodiment of the invention the adjustment is associated solely with the maxillary arch, the invention is well-suited for use with virtually any type of attachment to the mandibular arch.

A still further attribute to the invention is that it can be used not only as a sole treatment procedure, but in the case of multiple treatment procedures, can also be used in conjunction with other maxillary orthodontic appliances such as full bands, rapid palatal expansion, quad-helix, etc.

While one important advantage of the invention is its convenient adjustability by the treating professional, it has important functional attributes involving the treatment procedure. One of these attributes is that the attachment comprises a certain limited looseness in fit with respect to the maxillary arch which can be beneficial in minimizing the risk of breakage under certain patient-induced situations. In many cases it also allows for the use of a full length Herbst tube. Longer working parts of the Herbst mechanism are advantageous because they are less likely to disengage when the patient opens his or her mouth. The invention also has the advantage that in many patients it will be unnecessary to replace the Herbst tubes since the adjustment in the attachment to the maxillary arch performs a function which can otherwise be accomplished only by increasing the tube length.

Briefly, the attachment means depicted by the preferred embodiment of the invention as illustrated herein comprises a shaft passing through a standard headgear tube on the maxillary arch, typically in the molar region, and with the point of connection of the Herbst mechanism to the shaft being distal of the tube. An adjustable locking device is disposed on the shaft mesial of the tube. When the patient closes his or her mouth, the natural closure force results in corrective force being applied to the mandibular arch through the Herbst mechanism and its attachment. When the appliance is developing the corrective force, the locking device on the shaft abuts the tube, and it can therefore be appreciated that the locking device limits the extent of distal displacement of the point of connection of the Herbst mechanism from the tube. That portion of the shaft between the point of connection to the Herbst mechanism and the locking device has a mesial-distal slip fit through the tube and can rotate to some degree within the tube to provide a certain limited amount of looseness in operation just before the locking device abuts the tube. This looseness can be useful in promoting patient comfort and possibly preventing breakage in some situations.

During the course of treatment procedure, the locking device may be repositioned on the shaft to periodically reduce the amount by which the shaft can project distally from the tube. In other words the point at which the Herbst mechanism connects to the maxillary arch is increasingly moved mesially at periodic adjustment intervals, and this has the effect of increasing the length of the tube of the Herbst mechanism but without any need to actually replace the tube. The end result is that the appliance can be activated or adjusted during treatment to sequentially move the lower arch mesially, without the need for removing the appliance from the patient's mouth. It can be appreciated that this is a significant convenience for both the treating professional and the patient. Because the locking device is disposed mesial of the tube, it is conveniently accessible to the treating professional for adjustment.

The particular locking device is especially compact so that the attachment is quite compatible with a patient despite the fact that it may have to react substantial force when it bears against the headgear tube. The particular construction of the locking device which is used in the preferred embodiment has further advantages which will be detailed later on.

The foregoing features, advantages and benefits of the invention, along with additional ones, will be seen in the ensuing description and claims which should be considered in conjunction with the accompanying drawings. The drawings disclose a preferred embodiment of the invention according to the best mode contemplated at the present time in carrying out the invention.

DESCRIPTION OF THE PREFERRED EMBODIMENT

Figure 1:
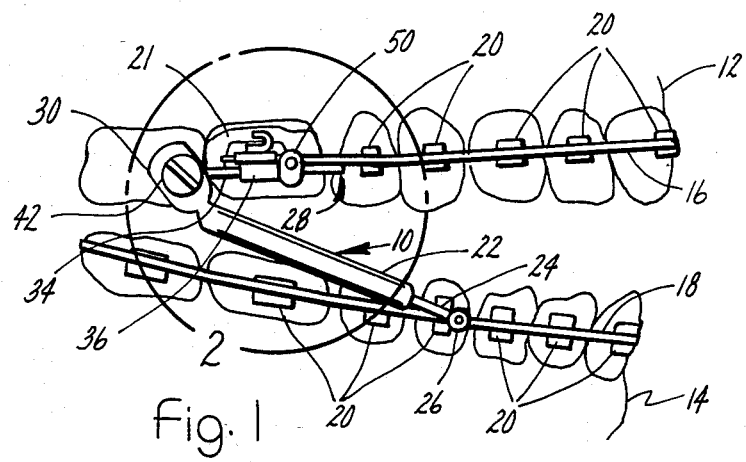
FIG. 1 is a buccal view of the Herbst mechanism operatively disposed between mandibular and maxillary arches and illustrates the improved attachment to the maxillary arch in accordance with principles of the invention.

The drawings illustrate one form of a Herbst mechanism 10 disposed between the maxillary arch 12 and the mandibular arch 14 in a patient. The illustration shows each arch 12, 14 to have an associated arch wire 16, 18 for the full extent of the arch, and each arch wire attached in conventional fashion to individual teeth of the arch by bonded brackets 20 except for the last molar tooth of the maxillary arch where the bracket 20 is attached to a molar band 21.

The illustrated Herbst mechanism 10 comprises a tube 22 and a shaft 24 which are telescopically engaged. Shaft 24 has an operative connection with arch wire 18 by any suitable sort of attachment mechanism 26, the illustrated one being a pivot joint. Tube 22 is attached to maxillary arch 12 by the improved attachment of the present invention, which is designated by the general reference numeral 28.

The end of tube 22 which connects to the maxillary arch via attachment 28 comprises an eyelet 30. The attachment 28 of the present invention comprises a member 32 having a shaft 34. Shaft 34 passes mesial-distally through a tube 36 on the bracket 20 which is affixed to molar band 21. The connection of eyelet 30 to member 32 takes place distally of tube 36.

Member 32 comprises a circular head 38 of the distal end of shaft 34. An axle 40 of circular cross section projects buccally of head 38. Eyelet 30 fits onto axle 40 and is retained thereon by means of a screw 42. This allows the tube to pivot on the axle.

Figure 3:
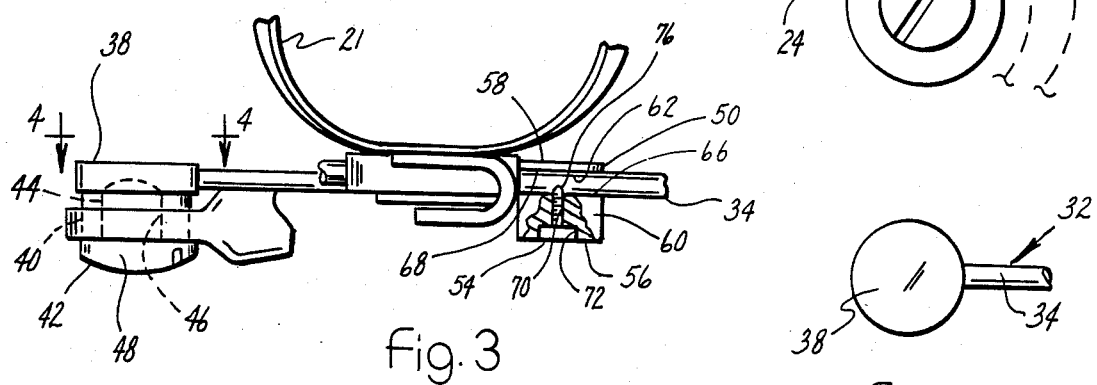
FIG. 3 is a top view of FIG. 2 with certain portions broken away for illustrative purposes.
Figure 4:
FIG. 4 is a fragmentary view taken in the direction of arrows 4—4 in FIG. 3.

Screw 42 comprises a threaded shank 44 which threads into a threaded hole 46 which extends into member 32 from the buccal end of axle 40. Screw 42 comprises a head 48 of a diameter greater than the hole in eyelet 30 to thereby prevent the eyelet from coming off axle 40. As can be seen in FIG. 3, it is desirable that the length of axle 44 exceed the thickness of eyelet 30 so that there is a limited amount of axial play of the eyelet on the axle.

Attachment 28 further comprises a locking device 50 locked on shaft 34 mesial of tube 36. Locking device 50 is adjustably positionable along the length of shaft 34 when unlocked. When locked, it forms a stop for forcefully abutting the mesial end of tube 36 with a distally directed force when the appliance is exerting a corrective force on the maxillary arch. This abutment position is shown in the drawing figures.

Because locking device 50 forms a stop, it limits the distal extension of shaft 34 from tube 36. In other words it is effective to establish the maximum distal position of the connection of the Herbst mechanism to the maxillary arch thereby setting a limit to the distal movement of the lower jaw.

Locking device 50 will typically abut tube 36 when the arches are closed. When the arches are open, there is a certain relaxation which allows either or both of: (1) a relative lengthening of the Herbst mechanism; and (2) a mesial displacement of shaft 34 through tube 36. Whether in any given patient either one, or the other, or both, will occur will depend upon the particular nature of the appliance and the particular condition of the patient. In any event the opening of the patient's mouth will relieve the force which is being exerted by the locking device, and this may be accompanied by some mesial displacement of shaft 34 through tube 36 whereby the locking device 50 is in fact moved out of abutment with tube 36.

The particular form of locking device 50 used in the preferred embodiment is especially advantageous for several reasons. The locking device is relatively compact, a desirable attribute for use in an orthodontic appliance, yet it is conveniently accessible by the treating professional.

The preferred embodiment of locking device 50 comprises a main body 52 and a screw 54. As viewed in FIG. 2, main body 50 has what may be considered as a generally oval shape. As viewed in FIG. 3, it can be seen to have a substantially uniform thickness. It may be considered to comprise end surfaces 56 and 58, the end surface 56 facing buccally, and a side surface 60 extending between the two end surfaces 56, 58.

The main body 52 is further provided with a walled slot 62 extending in side surface 60 in parallel relation to end surfaces 56 and 58, and with slot 62 being spaced more closely to surface 58 than surface 56. If viewed in cross section in the same direction as FIG. 2 the slot may be considered to be a somewhat semi-oval shape comprising a bottom wall 64 and sidewalls 66 and 68. Shaft 34 passes completely through main body 52, entering and exiting the main body at mesial and distal end portions of slot 62.

Main body 52 is provided with a threaded hole 70 into which the shank of screw 54 threads. A counterbore 72 is also provided. The arrangement is such that the tip 76 of the screw shank is disposed within slot 62 and the head of the screw is disposed within counterbore 72 so that the buccal facing end of the screw head is generally flush with surface 56. The screw can be advanced and retracted within threaded hole 70 via a tool (not shown) which is used to engage a non-circular hole 74 in the buccal facing end of tube screw head. The illustrated construction for hole 74 is a hexagonal socket. Thus a hexagonal tool is inserted into hole 74 to rotate the screw on the main body, and thereby be effective to move the tip of the screw more or less fully into slot 62 depending upon the amount of screw actuation by the tool.

The screw tip 76 has a frusto-conical shape, and the co-axis of the screw and threaded hole 70 are such that the screw tip engages shaft 34 at a location which is spaced from the co-axis of the screw and threaded hole. In other words it is the flank of the frusto-conical tip which is caused to bear against shaft 34 within slot 62.

When the screw is fully tightened, the interaction between the frusto-conical tip and shaft 34 is such that the locking device is securely locked onto the shaft because of the screw urging the shaft against the wall of the slot. If the screw is untightened, this releases the locking force whereby it is possible to slide the locking device along shaft 34.

It is to be observed that only a small amount of actuation of the screw is required in order to release the locking engagement of the locking device on the shaft. This is advantageous for adjustment purposes, yet the locking action of the device on the shaft is sufficient to react the forces exerted during usage of the appliance without slipping on the shaft.

It is also to be observed that by making the slot just wide enough for shaft 34, and by suitable arrangement of the screw tip, initial untightening of the screw still results in the screw overlying the shaft so that the locking device does not simply fall off. With the screw untightened, the locking device can be positioned to any appropriate location on shaft 34 which will produce a desired amount of distal extension of the shaft from the tube 36 when the locking device is abutting the mesial end of tube 36.

Figure 2:
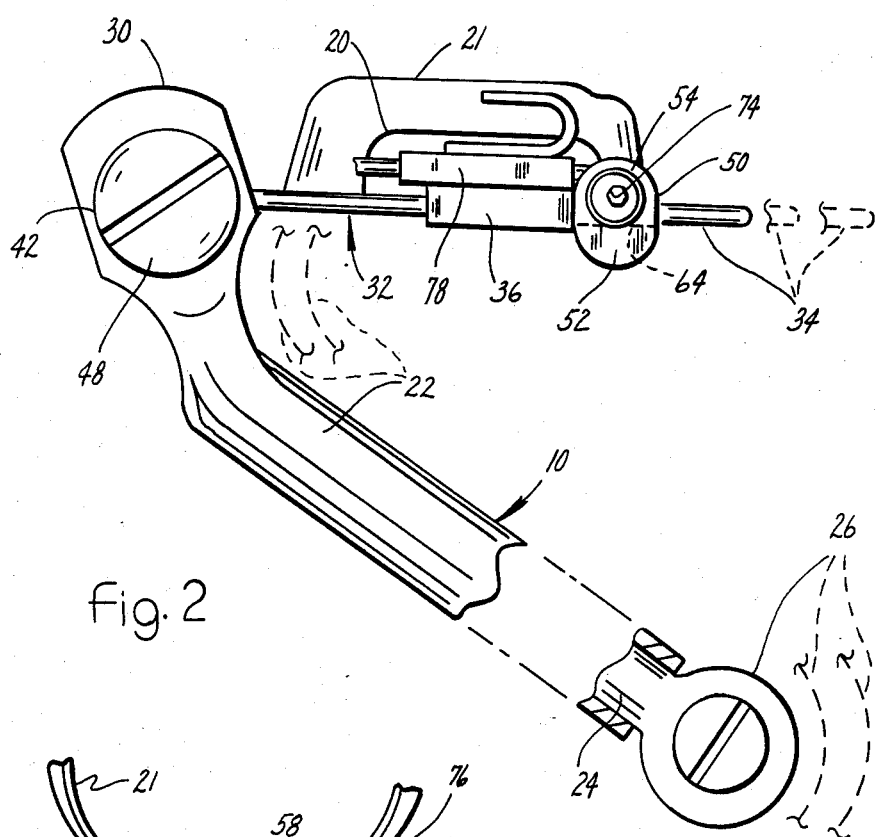
FIG. 2 is an enlarged view taken in circle 2 of FIG. 1 illustrating further detail, and with certain portions omitted for clarity.

As mentioned above, one important advantage of the invention is that it allows the treating professional to assemble the appliance extra-orally and then after the intra-oral placement, it is possible to conveniently adjust the appliance by simply positioning the locking device on shaft 34. In this regard the broken line positions depicted in FIG. 2 represent subsequent positions of adjustment whereby over the course of treatment procedure the amount of distal extension of shaft 34 from tube 36 is periodically reduced. The treatment results in anterior movement of the point of connection of the Herbst mechanism with the mandibular arch as that arch is moved anteriorly and the adjustment of the present invention is equivalent to a lengthening of the mechanism but without the need to actually lengthen the mechanism.

The attachment comprises further additional features of benefit. For one it will be observed that the oval shape of body 52 of locking device 50 results in a convex curved surface bearing against the end of tube 36 and although the amount of curvature is relatively small at the bearing point, it can be beneficial.

It will also be observed that not only is locking device 50 adjustable along the length of the shaft, but it is also possible to rotatably position locking device 50 about the axis of the shaft 34. This will be of advantage not only for ease of intra-oral adjustment, but also for the particular appliance shown wherein the arch wire 16 fits into a further tube 78 which overlies tube 36. With this arrangement the locking device can be positioned so that a portion of the arch wire passes through the top of the slot in overlying relationship to screw 54 free of any interference with the locking device. In FIG. 3, tube 78 is slightly offset from tube 36, and it will be appreciated that locking device 50 is appropriately positioned so that the arch wire passes through the slot even though the position of the locking device which has been illustrated in that FIG. 3 does not exactly show that position for purposes of clarity in illustrating the locking device details.

In the typical appliance there will be Herbst mechanisms on opposite sides of the arches. FIG. 1 illustrates the right hand mechanism and it will be appreciated that there is a complementary mechanism on the left hand side. It will have a similar type of attachment means to the maxillary arch.

While a preferred embodiment of the invention has been disclosed it will be appreciated that principles are applicable to other embodiments. For example, locking devices other than the illustrated one are contemplated within the broader aspects of the invention although it will be appreciated that the illustrated embodiment has many specific attributes. Moreover, although the illustrated embodiment comprises the locking device bearing against tube 36, it will be appreciated that abutment of the locking device could be with any portion of the means which affixes the tube to the arch. As noted earlier, the attachment is useful with various forms of Herbst mechanisms and with all types of mandibular attachments.

What is claimed is:

1. In an orthodontic appliance of the type having corrective means for cooperative association between maxillary and mandibular arches for translating natural closure of the arches into an anatomically anterior corrective force on the mandibular arch, the improvement for attaching the corrective means to the maxillary arch which comprises fixation means including a tube for affixation to the maxillary arch with the length of the tube disposed mesial-distally, a shaft of a length greater than that of the tube passing completely through the tube so as to project both mesially and distally from the tube and to be mesial-distally displaceable with a sliding fit through the tube, connection of said corrective means to that portion of the shaft which projects distally from the tube, and a stop on said shaft mesial of said tube which forcefully bears against said fixation means with a distally directed force when corrective force is being developed on the mandibular arch by the corrective means and which is selectively positionable on the shaft to set the amount of distal extension of said connection from said tube at which said stop forcefully bears against said fixation means.

2. The improvement set forth in claim 1 in which said stop comprises a releasable locking device on said shaft.

3. The improvement set forth in claim 2 in which said releasable locking device comprises a main body having an opening through which said shaft completely passes, and locking means on said main body selectively operable to operate the device to locked and released positions on said shaft.

4. The improvement set forth in claim 3 in which said locking means comprises a buccal facing, tool-receiving surface for receiving a tool used to operate the device to locked and released positions on said shaft.

5. The improvement set forth in claim 4 in which said locking means comprises a screw threaded into a coaxial threaded bore which intercepts said opening, said screw comprising an end opposite said tool-receiving surface which forcefully engages the shaft against said main body when the locking device is in the locked position.

6. The improvement set forth in claim 5 in which the co-axis of said threaded bore and screw is transverse to, but does not intersect, the axis of said shaft as the shaft passes through said opening, said end of said screw comprising a frusto-conically shaped tip which is arranged to bear against the shaft at a location spaced from the co-axis of the screw and threaded bore.

7. The improvement set forth in claim 3 in which said opening comprises a slot having a mesial end portion and a distal end portion and said shaft enters and exits said slot at the slot's mesial and distal end portions.

8. The improvement set forth in claim 2 in which said releasable locking device comprises a buccal facing, tool-receiving surface adapted for engagement by a tool to operate the device to locked and released positions.

9. The improvement set forth in claim 2 in which said releasable locking device comprises a main body having a walled slot extending into the main body from an external surface thereof and having a mesial-distal extent and said shaft passes mesial-distally completely through said slot, said shaft entering and exiting said main body at mesial and distal ends of said slot, a threaded bore in said main body extending from a buccal facing, external surface of the main body to intercept said slot, said threaded bore having an axis disposed above the axis of said shaft as the shaft passes through said main body, a screw threaded coaxially into said threaded bore and comprising a buccal facing, tool-receiving surface for reception of a tool which is used to rotate the screw and advance and retract same within said threaded bore, said screw comprising a shank end in the form of a frusto-conically shaped tip which is effective to bear against the shaft at a location which is spaced from the axis of the screw and force the shaft against the wall of the slot to lock the main body on the shaft.

10. The improvement set forth in claim 2 in which said locking device comprises a main body having a walled slot extending from an external surface thereof and having a mesial-distal extent, a portion of said shaft passing mesial-distally through said slot and further including an arch wire for association with the maxillary arch, at least a portion of said arch wire passing mesial-distally through said slot.

11. The improvement set forth in claim 10 in which said locking device comprises a locking means on said main body for selective operation in association with said shaft and slot to lock and release the device on the shaft.

12. The improvement set forth in claim 2 in which said shaft is a solid member of circular transverse cross section.

13. The improvement set forth in claim 2 in which said locking device is both angularly and mesial-distally positionable with respect to said shaft.

14. The improvement set forth in claim 1 in which said fixation means and stop are so arranged that the stop forcefully bears against a mesial end of said tube when corrective force is being developed on the mandibular arch by the corrective means.

15. The improvement set forth in claim 14 in which said stop comprises a main body with a convex curved surface which forcefully bears against said tube when corrective force is being developed on the mandibular arch by the corrective means.

16. The improvement set forth in claim 1 in which said shaft comprises a head at the shaft's distal end, said connection of said corrective means to that portion of the shaft which projects distally from the tube being to said head.

17. The improvement set forth in claim 16 in which an axle projects bucally from said head to provide a pivot for the connection of said corrective means to said shaft, and a screw threads into a threaded bore in said axle for keeping the connection on said axle.

18. The improvement set forth in claim 17 in which said shaft and tube are constructed and arranged to also provide for a certain amount of shaft rotation within the tube.

* * * * *